(12) United States Patent
Chew et al.

(10) Patent No.: US 7,120,480 B2
(45) Date of Patent: Oct. 10, 2006

(54) LED FORWARD VOLTAGE ESTIMATION IN PULSE OXIMETER

(75) Inventors: Bradford B. Chew, San Ramon, CA (US); Ethan Peterson, Castro Valley, CA (US); William Shea, Livermore, CA (US)

(73) Assignee: Nellcor Puritan Bennett Inc., Pleasanton, CA (US)

( * ) Notice: Subject to any disclaimer, the term of this patent is extended or adjusted under 35 U.S.C. 154(b) by 391 days.

(21) Appl. No.: 10/788,243

(22) Filed: Feb. 25, 2004

(65) Prior Publication Data

US 2005/0187450 A1    Aug. 25, 2005

(51) Int. Cl.
*A61B 5/00*      (2006.01)
(52) U.S. Cl. ..................................... 600/323
(58) Field of Classification Search ................ 600/310, 600/322, 323, 330
See application file for complete search history.

(56) References Cited

U.S. PATENT DOCUMENTS

| | | | |
|---|---|---|---|
| 4,802,486 A | 2/1989 | Goodman et al. | |
| 4,911,167 A | 3/1990 | Corenman et al. | |
| 4,928,692 A | 5/1990 | Goodman et al. | |
| 4,934,372 A | 6/1990 | Corenman et al. | |
| 5,351,685 A | 10/1994 | Potratz | |
| 5,368,026 A | 11/1994 | Swedlow et al. | |
| 5,590,652 A * | 1/1997 | Inai ............................ 600/323 |
| 5,662,106 A | 9/1997 | Swedlow et al. | |
| 5,713,355 A | 2/1998 | Richardson et al. | |
| 5,746,697 A | 5/1998 | Swedlow et al. | |
| 5,803,910 A | 9/1998 | Potratz | |
| 5,859,658 A | 1/1999 | Hammond | |
| 5,921,921 A | 7/1999 | Potratz et al. | |
| 5,924,979 A | 7/1999 | Swedlow et al. | |
| 6,226,539 B1 | 5/2001 | Potratz | |
| 6,356,774 B1 | 3/2002 | Bernstein et al. | |
| 6,560,470 B1 | 5/2003 | Pologe | |

FOREIGN PATENT DOCUMENTS

| | | |
|---|---|---|
| EP | 0477417 A1 | 9/1990 |
| WO | WO 03/068060 A | 8/2003 |

* cited by examiner

*Primary Examiner*—Eric Winakur
*Assistant Examiner*—Etsub Berhanu
(74) *Attorney, Agent, or Firm*—Fletcher Yoder P.C.

(57) ABSTRACT

An apparatus and method for determining if a forward voltage of an LED in a pulse oximeter is within a predetermined range. This is accomplished by measuring the current through the LED, and also by knowing the duty cycle of the pulse width modulator (PWM) drive signal to the LED.

9 Claims, 3 Drawing Sheets

LED FORWARD VOLTAGE ESTIMATION IN PULSE OXIMETER

BACKGROUND OF THE INVENTION

The present invention relates to oximeters, and in particular to controlling the LED voltage.

Pulse oximetry is typically used to measure various blood chemistry characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

The light sources, typically light emitting diodes (LEDs), need to be driven with current to activate them. In order to determine sensor failure, such as an open or shorted LED, the current through the LED can be measured. Typically, this is done with a feedback resistor across which the voltage is measured to determine if any current is flowing. If no current is flowing, there is assumed to be an open connection.

BRIEF SUMMARY OF THE INVENTION

The present invention provides an apparatus and method for determining if a forward voltage of an LED in a pulse oximeter is within a predetermined range. This is accomplished by measuring the current through the LED, and also by knowing the duty cycle of the pulse width modulator (PWM) drive signal to the LED.

In one embodiment, the determination of the forward voltage being within a predetermined range is done within a processor, which provides an error signal if the forward voltage is outside the range. The error signal could indicate, for example, a short or open connection in the LED sensor.

In one embodiment, the processor includes a proportional integral (PI) loop which generates the PWM signal from an error signal corresponding to the difference between the actual current and desired current delivered to the LED.

For a further understanding of the nature and advantages of the present invention, reference should be made to the following description taken in conjunction with the accompanying drawings.

DETAILED DESCRIPTION OF THE INVENTION

Oximeter Front-End

Figure 1:
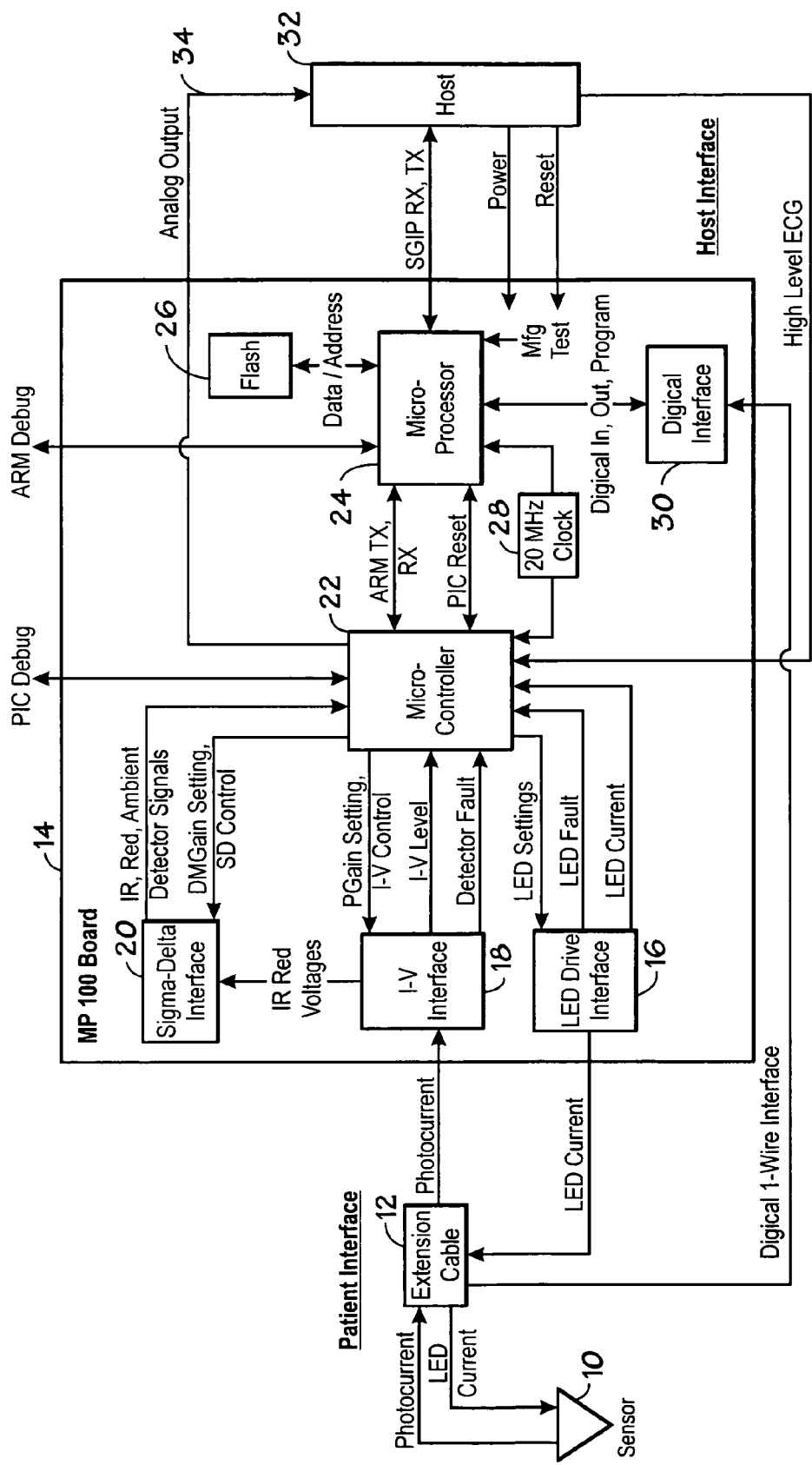
FIG. 1 is a block diagram of an oximeter incorporating the present invention.

FIG. 1 illustrates an embodiment of an oximetry system incorporating the present invention. A sensor 10 includes red and infrared LEDs and a photodetector. These are connected by a cable 12 to a board 14. LED drive current is provided by an LED drive interface 16. The received photocurrent from the sensor is provided to an I-V interface 18. The IR and red voltages are then provided to a sigma-delta interface 20 incorporating the present invention. The output of sigma-delta interface 20 is provided to a microcontroller 22 which includes a 10-bit A/D converter. Microcontroller 22 includes flash memory for a program, and SRAM memory for data. The oximeter also includes a microprocessor 24 connected to a flash memory 26. Finally, a clock 28 is used and an interface 30 to a digital calibration in the sensor 10 is provided. A separate host 32 receives the processed information, as well as receiving an analog signal on a line 34 for providing an analog display.

LED Drive Circuit

Figure 2:
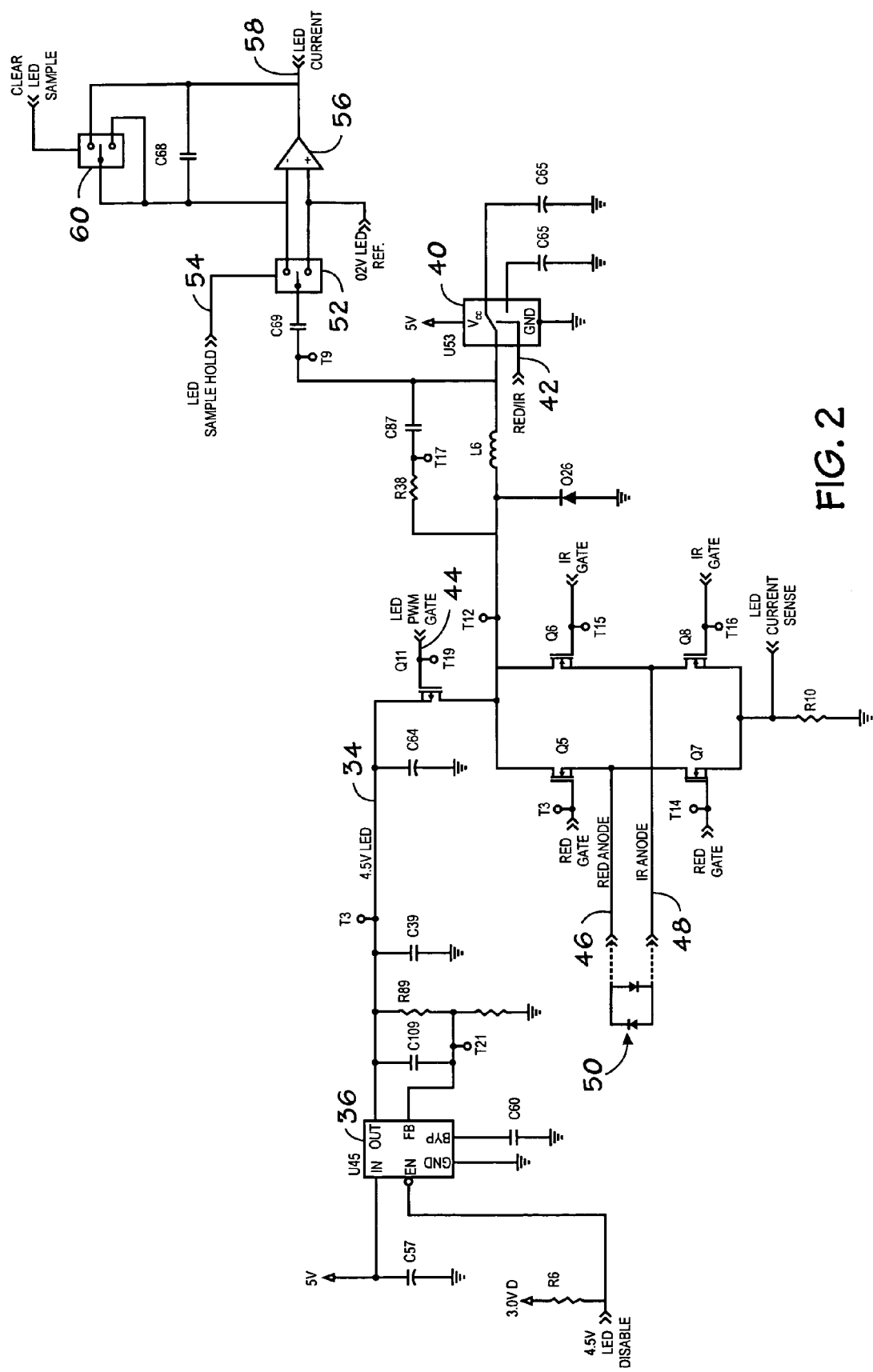
FIG. 2 is a circuit diagram of a LED drive circuit according to an embodiment of the present invention.

FIG. 2 is a circuit diagram of the LED drive circuit according to an embodiment of the invention, which forms a portion of LED drive interface 16 of FIG. 1. A voltage regulator 36 provides a voltage separate from the voltage supply for the overall oximeter circuitry. The output is provided as a 4.5 volt signal on line 38, with the level being set by the feedback resistor divider of resistors R89 and R90. The voltage on line 38 is provided to a FET transistor Q11 to an inductor L6. The current through inductor L6 is provided by a switch 40 to one of capacitors C65 and C66, which store charge for the red and IR LEDs, respectively. A red/IR control signal on line 42 selects the switch position under control of the oximeter processor. A control signal LED PWM gate on line 44 controls the switching of transistor switch Q11.

Once the capacitors are charged up, the control signal on line 44 turns off switch Q11 and current is provided from either capacitor C65 or C66, through switch 40 and inductor L6 to either the red anode line 46 or the IR anode line 48 by way of transistors Q5 and Q6, respectively. A signal "red gate" turns on transistor Q5, while its inverse, "/red gate" turns off transistor Q7. This provides current through the red anode line 46 to the back to back LEDs 50, with the current returning through the IR anode to transistor Q8 and through resistor R10 to ground. Transistor Q8 is turned on by the signal "/IR gate" while the inverse of this signal, "IR gate" turns off transistor Q6. The signals are reversed when the IR anode is to be driven, with the "IR gate" and "red gate" signals, and their inverses, changing state, so that current is provided through transistor Q6 to IR anode 48 and returns through red anode 46 and through transistor Q7 to resistor R10 and ground. The "LED current sense" signal is read for calibration purposes not relevant to the present invention.

When the current from the capacitor C65 or C66 is provided through inductor L6 to the LEDs, and that current is switched off at the desired time, transistor Q11 is turned on so that the remaining current during the transition can be dumped into capacitor C64. This addresses the fact that the FET transistor switching is not instantaneous. Subsequently, C64 will dump its current through Q11 and inductor L6 into the capacitors when they are recharged.

Resistor R38 and capacitor C67 are connected in parallel to inductor L6 to protect against signal spikes, and provide a smooth transition. Connected to inductor L6 is a sampling circuit with a switch 52 controlled by an LED sample hold signal on line 54 to sample the signals and provide them through an amplifier 56 to a "LED current" signal on line 58 which is read by the processor. An integrating capacitor C68 provides feedback for amplifier 56. A switch 60 responds to a "clear LED sample" signal to operate the switch to short out the capacitor between samples.

Operational amplifier 56 operates between 4.5 volts and ground. Thus, a voltage reference slightly above ground, of 0.2 volts, is provided as a voltage reference on pin 3.

The sample and hold circuit measures the voltage at node T18, between capacitor C69 and inductor L6, to determine the current. Capacitor C69 is 1/1000 of the value of capacitors C65 and C66. Thus, a proportional current is provided through C69, which is injected through switch 52 to integrating capacitor C68 to provide a voltage which can be measured at the output of amplifier 56 on line 58. The voltage measured by the processor on line 58 is used as a feedback, with the processor varying the width of the pulse delivered to transistor Q11 to selectively vary the amount of energy that's delivered to the capacitors 65 and 66, and then is eventually discharged to the LEDs 50. A PI (Proportional Integral) loop inside the processor then controls the PWM signal that controls Q11. This allows precise control of the LED intensity, allowing it to be maximized, if desired, without exceeding the desired limits.

The lower left of the diagram shows a "4.5 v LED disable" signal which is used by the microprocessor to turn off the voltage regulator 36 in certain instances. For example, diagnostics looking for shorts in a new sensor plugged in may turn off the voltage regulator if there is a problem with the LED line.

LED Voltage Determination

Figure 3:
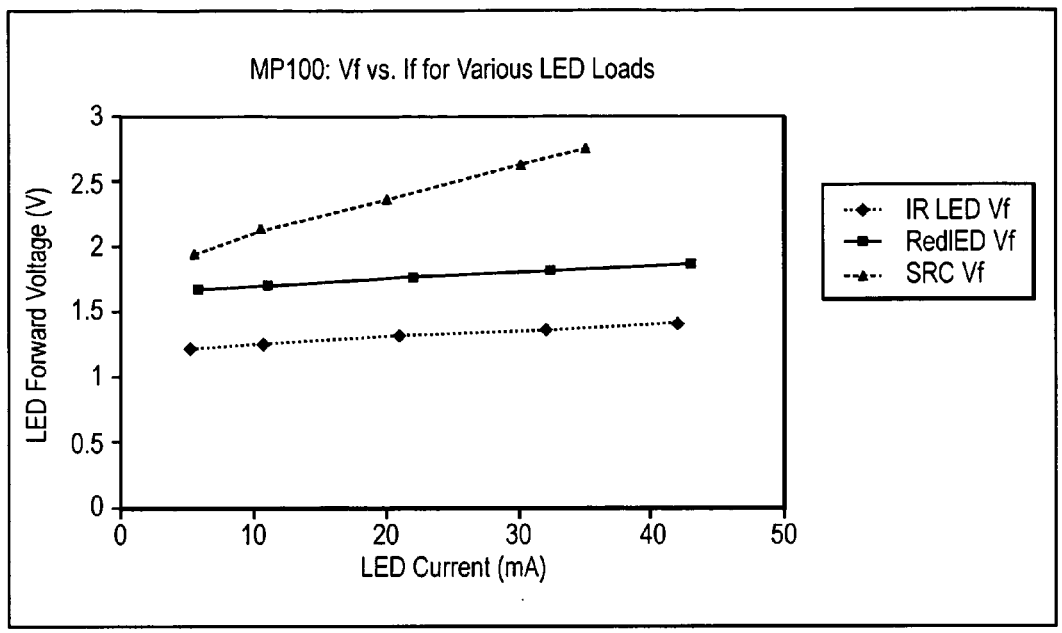
FIGS. 3 and 4 are graphs illustrating the forward voltage versus current and PWM duty cycle versus power, respectively, for an LED in an embodiment of the present invention.
Figure 4:
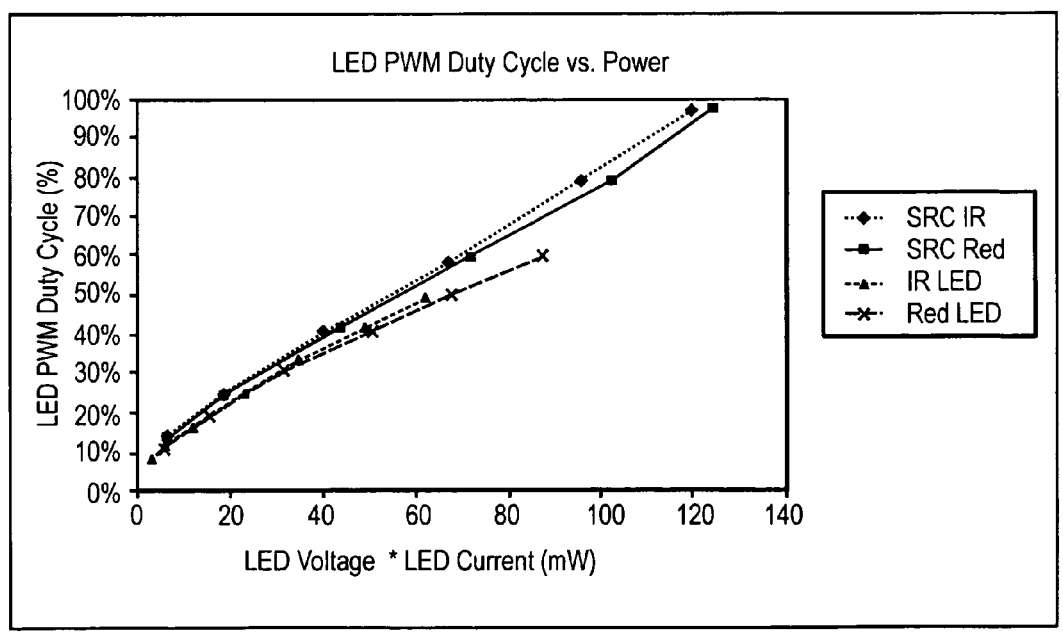

FIGS. 3 and 4 illustrate the properties discovered by the present inventors which allowed development of the present invention. FIG. 3 is a graph of LED forward voltage versus LED current. The three different graphs produce three different lines with three different slopes for different types of loads: an IR LED, a red LED and a functional tester (SRC) which has a diode and a resistor in series. As can be seen, measuring the current alone does not indicate what the LED forward voltage is unless one also knows the type of load, and has stored a curve such as that shown in FIG. 3.

FIG. 4 illustrates a plot of LED PWM duty cycle, which is the pulse width modulated drive signal for driving the LED. This is plotted on the vertical axis versus the power on a horizontal axis (LED voltage times LED current). As can be seen, for four different types of LED or SRC devices plotted, the plots are nearly identical with nearly identical slopes. From this recognition, the inventors determined that the voltage could be determined if one knows the PWM duty cycle and the current. The current is available from line 58 in FIG. 2, the LED current signal provided to the processor. The processor itself produces the PWM signal, and thus the processor has the two pieces of information needed to calculate the LED voltage for a particular LED, without knowing the type of LED. By using the information in FIG. 4, showing that the duty cycle is proportional by a constant to the power dissipated in the LED, a forward voltage can be derived.

In one embodiment, the PWM signal is generated using a PI (proportional integral) loop. This loop takes the formal equation set forth below:

$$y = Ae(t) + B\int e(t)dt$$

where:

A and B are constants e=error signal, difference between desired and actual current y=PWM signal In one embodiment, a PWM duty cycle generated by the processor is provided to a lookup table which stores the data in the graph of FIG. 4. The lookup table will produce the power dissipated as an output. This value can then be divided by the LED current as provided on line 58. The result of the division will be the forward voltage of the LED.

Alternately, in another embodiment, a lookup table can be eliminated and a comparison can be done of the duty cycle and the current. Since the duty cycle is equal to the current times the voltage times a constant, upper and lower ranges for the ratio of duty cycle/LED current can be established to indicate conditions such as a short circuit or open connection in the LED. Alternately, a series of ranges could be used, with an outer range indicating the short or open condition, and an inner range, in one example, indicating the desired operating range for the LED. For example, the oximeter may need to drive the LED harder, near its maximum current, for certain patients with weak pulse signals.

As will be understood by those with skill in the art, the present invention may be embodied in other specific forms without departing from the essential characteristics thereof. For example, the determination of forward voltage could be done entirely in hardware, rather than in software in a processor. Accordingly, the foregoing description is intended to be illustrative, but not limiting, of the scope of the invention which is set forth in the following claims.

What is claimed is:

1. A pulse oximeter comprising:
   at least one light emitting diode (LED) drive circuit;
   a current measuring circuit for measuring a current through the LED;
   a controller for generating a pulse width modulator (PWM) drive signal to the LED; and
   a processor, coupled to the controller and to the current measuring circuit, configured to determine if a forward voltage of the LED is within a predetermined range using a measurement of the current and the PWM signal.

2. The pulse oximeter of claim 1 wherein the processor is configured to provide an error signal if the forward voltage is outside the range.

3. The pulse oximeter of claim 1 wherein the processor is configured to calculate a ratio of the PWM drive signal to the measurement of the current to determine if the ratio is within an acceptable voltage range.

4. The pulse oximeter of claim 1 wherein the processor includes a proportional integral (PI) loop which generates the PWM signal from a current error signal reflecting a difference between the measurement of the current and a desired current.

5. A pulse oximeter comprising:
at least one light emitting diode (LED) drive circuit;
a current measuring circuit for measuring a current through the LED;
a controller for generating a pulse width modulator (PWM) drive signal to the LED;
a processor, coupled to the controller and to the current measuring circuit, configured to determine if a forward voltage of the LED is within a predetermined voltage range using a measurement of the current and the PWM signal, by calculating a ratio of the PWM drive signal to the measurement of the current to determine if the ratio is within an acceptable voltage range;
wherein the processor is configured to provide an error signal if the forward voltage is outside the voltage range; and
wherein the processor includes a proportional integral (PI) loop which generates the PWM signal from a current error signal reflecting a difference between the measurement of the current and a desired current.

6. A method for operating a pulse oximeter comprising:
providing a current using at least one light emitting diode (LED) drive circuit;
measuring a current through the LED;
generating a pulse width modulator (PWM) drive signal to the LED;
determining if a forward voltage of the LED is within a predetermined range using a measurement of the current and the PWM signal; and
providing an indication if the forward voltage is outside the range.

7. The method of claim 6 further comprising calculating a ratio of the PWM drive signal to the measurement of the current to determine if the ratio is within an acceptable voltage range.

8. The method of claim 6 further comprising using a proportional integral (PI) loop to generate the PWM signal from a current error signal reflecting a difference between the measurement of the current and a desired current.

9. A method for operating a pulse oximeter comprising:
providing a current using at least one light emitting diode (LED) drive circuit;
measuring a current through the LED;
generating a pulse width modulator (PWM) drive signal to the LED;
determining if a forward voltage of the LED is within a predetermined voltage range using a measurement of the current and the PWM signal, by calculating a ratio of the PWM drive signal to the measurement of the current to determine if the ratio is within an acceptable voltage range;
providing an error signal if the forward voltage is outside the voltage range; and
using a proportional integral (PI) loop to generate the PWM signal from a current error signal reflecting a difference between the measurement of the current and a desired current.

* * * * *

UNITED STATES PATENT AND TRADEMARK OFFICE
CERTIFICATE OF CORRECTION

| | | |
|---|---|---|
| PATENT NO. | : 7,120,480 B2 | Page 1 of 1 |
| APPLICATION NO. | : 10/788243 | |
| DATED | : October 10, 2006 | |
| INVENTOR(S) | : Bradford B. Chew et al. | |

It is certified that error appears in the above-identified patent and that said Letters Patent is hereby corrected as shown below:

Title Page, item (75) of the page, please replace the second inventor's surname "Peterson" with --Petersen--.

Signed and Sealed this

Twenty-sixth Day of December, 2006

JON W. DUDAS
*Director of the United States Patent and Trademark Office*